United States Patent [19]

Behre et al.

[11] Patent Number: 4,973,758

[45] Date of Patent: Nov. 27, 1990

[54] PROCESS FOR THE PREPARATION OF 1,5-DIHYDROXYNAPHTHALENE AND 1,5-DIAMINONAPHTHALENE

[75] Inventors: Horst Behre, Odenthal; Lothar Jakob, Wolfratshausen; Heinz U. Blank, Odenthal; Dietmar Mayer, Bergisch Gladbach; Roland Busse, Burscheid, all of Fed. Rep. of Germany

[73] Assignee: Bayer Aktiengesellschaft, Leverkusen, Fed. Rep. of Germany

[21] Appl. No.: 439,757

[22] Filed: Nov. 21, 1989

[30] Foreign Application Priority Data

Dec. 2, 1988 [DE] Fed. Rep. of Germany ....... 3840618

[51] Int. Cl.$^5$ ........................................... C07C 209/18
[52] U.S. Cl. .................................................... 564/394
[58] Field of Search ........................................ 564/394

[56] References Cited

U.S. PATENT DOCUMENTS

| 455,442 | 7/1891 | Schmid | 564/394 |
|---|---|---|---|
| 2,363,819 | 11/1944 | Glahn et al. | 564/394 |

FOREIGN PATENT DOCUMENTS

| 0117471 | 1/1901 | Fed. Rep. of Germany | 564/394 |
|---|---|---|---|
| 0451348 | 7/1936 | United Kingdom | 564/394 |

Primary Examiner—Glennon H. Hollrah
Assistant Examiner—Susan P. Treanor
Attorney, Agent, or Firm—Sprung, Horn, Kramer & Woods

[57] ABSTRACT

The characteristic of the improved process for the preparation of 1,5-dihydroxynaphthalene and 1,5-diaminonaphthalene is to carry out the alkaline pressure hydrolysis of the disodium salt of naphthalene-1,5-disulphonic acid at temperatures from 270° to 290° C. and under 14 to 20 bar using an excess of sodium hydroxide solution such that the molar ratio NaOH/disodium salt of naphthalenesulphonic acid is at least 12:1. The 1,5-dihydroxynaphthalene which is obtained in this manner, without hazard and in substantially higher purity, is then aminated with ammonia in the presence of ammonium bisulphite to give 1,5-diaminonaphthalene, it being possible to achieve a further increase in the degree of purity of the 1,5-diaminonaphthalene by increasing the molar ratio $NH_3$/1,5-dihydroxynaphthalene to at least 6:1.

6 Claims, No Drawings

PROCESS FOR THE PREPARATION OF 1,5-DIHYDROXYNAPHTHALENE AND 1,5-DIAMINONAPHTHALENE

The invention relates to an improved process for the preparation of 1,5-diaminonaphthalene by alkaline pressure hydrolysis of the disodium salt of naphthalene-1,5-disulphonic acid and subsequent amination, by means of ammonia in the presence of ammonium bisulphite, of the 1,5-dihydroxynaphthalene obtained in the pressure hydrolysis, to give 1,5-diaminonaphthalene, and for the preparation of 1,5-dihydroxynaphthalene, the intermediate product obtained in the first stage of the process of preparation.

1,5-Dihydroxynaphthalene and 1,5-diaminonaphthalene are important intermediate products for the preparation of dyestuffs. 1,5-Diaminonaphthalene is also an important intermediate product of the preparation of polyurethanes. Since 1,5-diaminonaphthalene of high purity is required for the preparation of dyestuffs and for further processing to give 1,5-naphthylene diisocyanate (→polyurethanes), those skilled in the art have been intensively concerned with the development of processes for the preparation of 1,5-diaminonaphthalene which afford the product in good yields and in the required purity.

There are two different processes for the industrial preparation of 1,5-diaminonaphthalene:

A: the nitration of naphthalene followed by reduction of the dinitronaphthalene;

B: the amination with ammonia in the presence of ammonium sulphite of the 1,5-dihydroxynaphthalene obtained by bake-fusion from the disodium salt of naphthalene-1,5-disulphonic acid (see German Patent Specification No. 117,471; Ullmann's Encyklopädie der technischen Chemie ("Ullmann's Encyclopaedia of Industrial Chemistry"), 4th edition, volume 17, pages 107/108).

Process A has the serious disadvantage that, since a mixture of 1,8-dinitronaphthalene and 1,5-dinitronaphthalene containing the two isomers in a ratio of about 2:1 is formed in the nitration of naphthalene (see Houben-Weyl, 4th edition, volume 10/1, page 494), a separation into the isomers is required and that this separation of the isomers is associated with considerable expense and with the inevitable production of large amounts of 1,8-dinitronaphthalene.

Owing to the said disadvantages of process A, process B is generally preferred in industry. Hitherto the 1,5-dihydroxynaphthalene required for the preparation of 1,5-diaminonaphthalene by process B has been prepared by bake-fusion, that is to say by fusing naphthalene-1,5-disulphonic acid (disodium salt) with sodium hydroxide. Admittedly attempts have also been made to replace bake-fusion by a pressure-fusion, that is to say by heating the disodium salt of naphthalene-1,5-disulphonic acid under pressure with 50% strength sodium hydroxide solution (=alkaline pressure hydrolysis). This procedure was, however, given up for safety reasons, after accidents had taken place when using it on several occasions (see P.B. Report No. 74,197, pages 54–55; Ullmanns Encyklopädie der technischen Chemie ("Ullmann's Encyclopaedia of Industrial Chemistry"), 4th edition, volume 17, page 87).

It has now been found that the disodium salt of naphthalene-1,5-disulphonic acid can be converted without hazard into 1,5-dihydroxynaphthalene by pressure fusion, if the molar ratio NaOH/disodium salt of naphthalene-1,5-disulphonic acid in the alkaline pressure hydrolysis is substantially increased, that is to say from 7.8:1 to at least 12:1. It has been found that not only is it possible to carry out the pressure hydrolysis without a safety risk when using this excess of NaOH, but also that the quality of the 1,5-dihydroxynaphthalene obtained is, surprisingly, substantially improved as a result of this measure. As a result of the alkaline pressure hydrolysis (pressure fusion) using the excess of sodium hydroxide according to the invention, the 1,5-dihydroxynaphthalene obtained has a content of tarry constituents (higher-molecular by-products insoluble in chlorobenzene) which falls to a fraction of the content of tarry constituents exhibited by the 1,5-dihydroxynaphthalene obtained by bake-fusion or by pressure fusion with customary amounts of sodium hydroxide. These tarry constituents are carried over in the amination of 1,5-dihydroxynaphthalene to give 1,5-diaminonaphthalene and hitherto have had to be removed from the latter by involved purification processes, for example sublimation of the crude 1,5-diaminonaphthalene. Using the 1,5-dihydroxynaphthalene prepared by pressure hydrolysis with the excess of sodium hydroxide according to the invention gives a 1,5-diaminonaphthalene which has such a low content of tarry constituents that it needs no further purification before being processed further, for example to give 1,5-naphthylene diisocyanate.

The invention therefore relates to a process for the preparation of 1,5-diaminonaphthalene by alkaline pressure hydrolysis of the disodium salt of naphthalene-1,5-disulphonic acid with excess sodium hydroxide at temperatures from 270° to 290° C. and under pressures from 14 to 20 bar and by amination with ammonia in the presence of ammonium bisulphite of the 1,5-dihydroxynaphthalene obtained in the pressure hydrolysis, which process is characterized in that the sodium hydroxide for the alkaline pressure hydrolysis is used in an excess such that the molar ratio NaOH/disodium salt of naphthalene-1,5-disulphonic acid is at least 12:1, preferably 14:1 to 18:1 and particularly preferably 15:1 to 17:1.

At the same time, however, the invention also relates to the process for the preparation of 1,5-dihydroxynaphthalene by alkaline pressure hydrolysis of the disodium salt of naphthalene-1,5-disulphonic acid with excess sodium hydroxide at temperatures from 270° to 290° C. and under pressure from 14 to 20 bar, which process is characterized in that the sodium hydroxide for the alkaline pressure hydrolysis is used in an excess such that the molar ratio NaOH/disodium salt of naphthalene-1,5-disulphonic acid is at least 12:1, preferably 14:1 to 18:1 and particularly preferably 15:1 to 17:1.

It has also been found that the quality of the 1,5-diaminonaphthalene can be improved further by means of the following new measures in the amination of the 1,5-dihydroxynaphthalene with ammonia in the presence of ammonium bisulphite:

(a) using a greater excess of ammonia than hitherto in the amination and employing ammonia and 1,5-dihydroxynaphthalene in molar ratios of at least 6:1, preferably 6.5:1 to 12:1 and particularly preferably 7:1 to 9:1; and —above all—

(b) when the amination reaction is complete, adding at least 1.5 mol, preferably 1.55 to 2 mol, and particularly preferably 1.6 to 1.8 mol, of sodium hydroxide per mol of 1,5-dihydroxynaphthalene employed to the reaction mixture at temperatures of at least 145° C., preferably 150° to 180° C.

These two new measures in the amination have the effect that the 1,5-diaminonaphthalene obtained is virtually free from 1-amino-5-hydroxynaphthalene, which causes serious problems in its further processing.

The invention therefore relates preferably to a process for the preparation of 1,5-diaminonaphthalene by alkaline pressure hydrolysis of the disodium salt of naphthalene-1,5-disulphonic acid with excess sodium hydroxide at temperatures from 270° to 290° C. and under pressures from 14 to 20 bar and by amination with ammonia in the presence of ammonium bisulphite at an elevated pressure and an elevated temperature of the 1,5-dihydroxynaphthalene obtained in the alkaline pressure hydrolysis, which process is characterized in that (a) the sodium hydroxide for the alkaline pressure hydrolysis is used in an excess such that the molar ratio NaOH:disodium salt of naphthalene-1,5-disulphonic acid is at least 12:1, preferably 14:1 to 18:1 and particularly preferably 15:1 to 17:1;

(b) the amination is carried out with an excess of ammonia such that the molar ratio ammonia/1,5-dihydroxynaphthalene is at least 6:1, preferably 6.5:1 to 12:1 and particularly preferably 7:1 to 9:1; and (c) when the amination reaction is complete, at least 1.5 mol, preferably 1.55 to 2 mol, and particularly preferably 1.6 to 1.8 mol, of NaOH per mol of 1,5-dihydroxynaphthalene employed are added to the reaction mixture at temperatures of at least 145° C., preferably 150° to 180° C.

Instead of being employed as such, the disodium salt of naphthalene-1,5-disulphonic acid required for the alkaline pressure hydrolysis can also be produced in situ in the hydrolysis mixture from free naphthalene-1,5-disulphonic acid or the tetrahydrate thereof and the amount of sodium hydroxide required for the neutralization of the free acid.

Working up of the hydrolysis mixture is effected in a manner which is in itself known, for example by diluting the alkaline reaction mixture with water, neutralizing the alkaline solution with a mineral acid, for example hydrochloric acid or sulphuric acid, and mechanically removing (by filtration or centrifugation) the precipitated 1,5-dihydroxynaphthalene.

The working up of the amination mixture present after the addition of sodium hydroxide and the isolation of the 1,5-diaminonaphthalene is also effected in a manner which is in itself known, for example by distilling off the unreacted ammonia in the form of an aqueous ammonia solution from the reaction mixture and removing (filtering off or centrifuging off) the precipitated 1,5-diaminonaphthalene.

The quality of the 1,5-diaminonaphthalene obtained by the process according to the invention corresponds to that of purified 1,5-diaminonaphthalene. The 1,5-diaminonaphthalene obtained in accordance with the invention can, therefore, be reacted without further purification to give 1,5-naphthalene diisocyanate in high yields by phosgenation. Since the 1,5-diaminonaphthalene obtained in accordance with the invention contains no tarry constituents, the 1,5-naphthalene diisocyanate prepared from it also contains no tarry by-products which could lead to difficulties in the preparation of the diisocyanate.

EXAMPLE 1

A mixture of 374 g (=1.0 mol) of naphthalene-1,5-disulphonic acid (disodium salt) (89% strength by weight product), 600 g of sodium hydroxide (15.0 mol) and 237 g of water is heated with stirring to 285° C. in a 1.3 liter nickel autoclave in the course of 2.5 to 3 hours, and is kept at this temperature for 2 hours. After the contents of the autoclave have been cooled to about 120° C., 400 g of water are pumped in. The mixture, which is at about 80° to 90° C., is transferred from the autoclave into another reaction vessel and is diluted there with about 1200 g of water to a total weight of about 2800 g. The diluted reaction mixture is introduced with stirring into 500 g of water at 80° C. and in the course of one hour, simultaneously with 1470 g of 50% strength by weight sulphuric acid. The resulting mixture is stirred for a further hour at 80° C., cooled to 60° C. in the course of 2 hours and then stirred for one hour at 60° C. The 1,5-dihydroxynaphthalene is filtered off at 60° C., washed with three times 500 g of hot water (60° C.) and finally dried in vacuo.

158 g (=96.6% of theory, relative to naphthalene-1,5-disulphonic acid employed) are obtained.

Composition:

98.1% by weight of 1,5-dihydroxynaphthalene, 0 to 0.1% by weight of 5-hydroxynaphthalene-1-sulphonic acid, 0.1 to 0.5% by weight of 1-naphthol, remainder up to 100% by weight: water, $Na_2SO_4$, $Na_2SO_3$ and unknown by-products.

A mixture of 130 g of 1,5-dihydroxynaphthalene (98.1% strength by weight=0.8 mol), 102 g of ammonia (6.0 mol), 52 ml of ammonium bisulphite solution (490 g of $SO_2$ per liter=0.4 mol) and 449 g of water is heated with stirring to 155° C. in a 1.3 liter titanium autoclave and is stirred at this temperature for 4 hours. 102 g of 50% strength by weight sodium hydroxide solution (1.28 mol of NaOH) are then pumped in with stirring at 155° C. The reaction mixture is cooled to 70° C. and is stirred for a further hour at this temperature. The precipitated 1,5-diaminonaphthalene is then filtered off and washed several times with water at 70° C. Drying in vacuo gives 110 g of 1,5-diaminonaphthalene (=86% of theory, relative to 1,5-dihydroxynaphthalene employed).

Composition:

99.0% by weight of 1,5-diaminonaphthalene, 0.2% by weight of 1-aminonaphthalene, 0.0–0.05% by weight of 1-amino-5-hydroxynaphthalene, 0.4% by weight of low-molecular by-products, 0.1% by weight of ash, 0.1% by weight of water and 0.2% by weight of by-products insoluble in chlorobenzene.

EXAMPLE 2

A mixture of 369.2 g (=1.0 mol) of naphthalene-1,5-disulphonic acid (tetrahydrate) (97.5% strength by weight product), 680 g of sodium hydroxide (17.0 mol) and 165 g of water is heated with stirring to 285° C. in a 1.3 liter nickel autoclave in the course of 2.5 to 3 hours, and are kept at this temperature for 2 hours. When the contents of the autoclave have been cooled to about 120° C., 400 g of water are pumped in. The contents of the autoclave are transferred at a temperature of 80° C. to 90° C. into an open reaction vessel and are there diluted with 1200 g of water to a total weight of about 2800 g. The diluted reaction mixture is introduced at 80° C. and in the course of 1 hour into 500 g of water, at the same time as 1470 g of 50% strength by weight sulphuric acid; the mixture is stirred for 1 hour at 80° C., then cooled to 60° C. in the course of 2 hours and stirred for 1 hour at 60° C. The 1,5-dihydroxynaphthalene is filtered off at 60° C., washed with three times 500 g of hot water (60° C.) and dried in vacuo. 158 g (96.6% of theory, relative to naphthalene-1,5-disulphonic acid employed) are obtained.

Composition:

98.1% by weight of 1,5-dihydroxynaphthalene, 0 to 0.1% by weight of 5-hydroxynaphthalene-1-sulphonic acid and 0.1 to 0.5% by weight of 1-naphthol.

A mixture of 130.5 g of 1,5-dihydroxynaphthalene (98.1% strength by weight=0.8 mol), 136 g of ammonia (8.0 mol), 52 ml of ammonium bisulphite solution (490 g of $SO_2$ per liter=0.4 mol) and 449 g of water are heated with stirring to 155° C. in a 1.3 liter titanium autoclave and are stirred at this temperature for 4 hours. 140 g of 50% strength by weight sodium hydroxide solution (1.75 mol of NaOH) are then pumped in at the same temperature. The reaction mixture is cooled to 70° C. and is stirred for a further hour at this temperature. The 1,5-diaminonaphthalene is then filtered off, washed several times with water at 70° C. and finally dried in vacuo.

110 g of 1,5-diaminonaphthalene (86% of theory, relative to 1,5-dihydroxynaphthalene employed) are obtained.

Composition:

99% by weight of 1,5-diaminonaphthalene, 0.2% by weight of 1-aminonaphthalene, 0.0% by weight of 1-amino-5-hydroxynaphthalene, 0.3% by weight of low-molecular by-products, 0.1% by weight of ash, 0.1% by weight of water and 0.3% by weight of by-products insoluble in chlorobenzene.

What is claimed is:

1. In the process for the preparation of 1,5-diaminonaphthalene which comprises subjecting the disodium salt of naphthalene-1,5-disulphonic acid to an alkaline pressure hydrolysis with excess sodium hydroxide at temperatures from 270° to 290° C. and under a pressure of from 14 to 20 bar and subsequently aminating the 1,5-dihydroxynaphthalene obtained in the pressure hydrolysis with ammonia in the presence of ammonium bisulphite the improvement which comprises using the sodium hydroxide for the alkaline pressure hydrolysis in an excess such that the molar ratio NaOH/disodium salt of naphthalene-1,5-disulphonic acid is at least 12:1.

2. The process of claim 1, wherein the molar ratio NaOH/disodium salt of naphthalene-1,5-disulphonic acid is 14:1 to 18:1.

3. The process of claim 1, wherein the amination is carried out with an excess of ammonia such that the molar ratio ammonia/1,5-dihydroxynapthalene is at least 6:1 and that, when the amination reaction is complete, at least 1.5 mol of NaOH per mol of 1,5-dihydroxynaphthalene employed is added to the reaction mixture at a temperature of at least 145° C.

4. The process of claim 3, wherein the molar ratio ammonia/1,5-dihydroxynaphthalene is 6.5:1 to 12:1 and that 1.55 to 2 mol of NaOH per mol of 1,5-dihydroxynaphthalene employed are added to the reaction mixture at a temperature of 150° to 180° C.

5. In the process for the preparation of 1,5-dihydroxynaphthalene which comprises subjecting the disodium salt of naphthalene-1,5-disulphonic acid to an alkaline pressure hydrolysis with excess sodium hydroxide at temperatures from 270° to 290° C. and under pressures from 14 to 20 bar the improvement which comprises using the sodium hydroxide for the alkaline pressure hydrolysis in an excess such that the molar ratio NaOH/disodium salt of naphthalene-1,5-disulphonic acid is at least 12:1.

6. The process of claim 5 wherein the molar ratio NaOH/disodium salt of naphthalene-1,5-disulphonic acid is 14:1 to 18:1.

* * * * *